United States Patent [19]

Lo et al.

[11] Patent Number: 5,534,413
[45] Date of Patent: Jul. 9, 1996

[54] ADHERENT AND INVASIVE MYCOPLASMA

[75] Inventors: Shyh-Ching Lo, Potomac; Richard Y. Wang, Bethesda, both of Md.; Michael M. Hayes, Alexandria, Va.

[73] Assignee: American Registry of Pathology, Washington, D.C.

[21] Appl. No.: 57,168

[22] Filed: May 4, 1993

Related U.S. Application Data

[60] Division of Ser. No. 800,370, Dec. 2, 1991, Pat. No. 5,215,914, and a continuation-in-part of Ser. No. 710,361, Jun. 6, 1991, Pat. No. 5,242,820, which is a continuation-in-part of Ser. No. 265,920, Nov. 2, 1988, abandoned, which is a continuation-in-part of Ser. No. 875,535, Jun. 18, 1986, abandoned.

[51] Int. Cl.$^6$ .............................. C12Q 1/04; C07K 16/12; G01N 33/569
[52] U.S. Cl. .......................... 435/7.32; 435/7.1; 435/870; 435/974; 435/975; 530/389.5
[58] Field of Search .................................. 435/5, 7.1, 870, 435/253.1, 7.32, 975; 530/389.5

[56] References Cited

PUBLICATIONS

Hakkarainen et al, "Serological Responses to Mycoplasmas in HIV–Infected and Non–Infected Individuals" AIDS 6:1287–1292, 1992.

Primary Examiner—Christine M. Nucker
Assistant Examiner—Julie Krsek-Staples
Attorney, Agent, or Firm—Venable, Baetjer, Howard & Civiletti

[57] ABSTRACT

The present invention relates to a novel mycoplasma isolated from the urine of patients with AIDS. The mycoplasma has unique morphological and pathobiological properties. The invention also relates to the antigens and antibodies of the novel mycoplasma, and methods of detection utilizing these antigens and antibodies. Antigenically and genetically, the mycoplasma is distinct from all other known mycoplasmas.

5 Claims, 9 Drawing Sheets

ADHERENT AND INVASIVE MYCOPLASMA

RELATED DISCLOSURES

This application is a division of application Ser. No. 800,370, filed Dec. 2, 1991, now U.S. Pat. No. 5,215,914, and a continuation-in-part of U.S. patent application Ser. No. 07/710,361, filed Jun. 6, 1991, now U.S. Pat. No. 5,242,820, which is a continuation-in-part of U.S. patent application Ser. No. 265,920, filed Nov. 2, 1988, now abandoned, which is a continuation-in-part of U.S. patent application Ser. No. 875,535, filed Jun. 18, 1986, now abandoned.

BACKGROUND OF THE INVENTION

Field of the Invention

The present invention relates to a novel strain of mycoplasma isolated from a patient with AIDS. The mycoplasma does not appear to be related to any other species of human or animal mycoplasma. This novel mycoplasma is referred to hereinafter as *M. penetrans*.

The invention also relates to use of the mycoplasma *M. penetrans* in detecting specific antibodies in sera of patients with AIDS or sub-acute and acute fulminant systemic diseases and/or animals and its use as a vaccine against infection by the mycoplasma. The invention further relates to *M. penetrans*-specific antibodies and cross-reactive *M. penetrans* antibodies (i.e. antibodies to homologous antigenic determinants), including monoclonal antibodies of each, which are useful in detecting *M. penetrans* antigens in infected tissues and specimens of patients or animals. The invention also relates to *M. penetrans* DNA probes which are useful in detecting *M. penetrans* genetic materials in infected tissues, blood or body fluids of patients or animals. *M. penetrans* genetic materials may also be detected in infected humans or animals by using *M. penetrans* DNA sequences or a homologous *M. penetrans* DNA sequence and the polymerase chain reaction ("PCR") (U.S. Pat. No. 4,683,202 incorporated herein by reference).

The ability to monitor AIDS or other acute fulminant systemic disease status can be of great value. In addition to improving prognostication, knowledge of the disease status allows the attending physician to select the most appropriate therapy for the individual patient, e.g. highly aggressive or less aggressive therapy regimens. Because of patient distress caused by more aggressive therapy regimens, it is desirable to distinguish those patients requiring such therapies.

*Mycoplasma* is a genus of cell wall-less sterol-requiring, catalase-negative pathogens commonly found in the respiratory and urogenital tracts of man and other animals. The cells of *Mycoplasma* are typically non-motile and pleomorphic, ranging from spherical, ovoid or pear-shaped to branched filamentous forms. Filaments are the typical forms in young cultures under optimal conditions, which subsequently transform into chains of coccoid cells which later break up into individual cells that are capable of passing through membrane filters of pore size 0.45 µm or even 0.22 µm.

A trilaminar cytoplasmic membrane contains sterols, phospholipid and proteins. Therefore, the cells are generally susceptible to polyene antibiotics and to lysis by digitonin.

Replication of the *Mycoplasma* genome may precede cytoplasmic division resulting in multinucleate filaments before individual cells are delimited by constriction. Budding can also occur.

Most *Mycoplasma* species are facultatively anaerobic, and all known species are chemoorganotrophic. The fermentative species of *Mycoplasma* utilize sugars such as glucose, while non-fermentative species can hydrolyze arginine. Only a few species of mycoplasma can utilize both glucose and arginine to grow.

Known mycoplasmas may be grown on complex media, such as Hayflick medium, while fastidious mycoplasmas may be grown on diphasic SP-4 medium. The colonies are usually of the "fried egg" type, i.e., an opaque, granular central region, embedded in the agar, surrounded by non-granular surface growth. The optimal growth temperature of mammalian strains is 36°–37° C.

Many species of *Mycoplasma* produce weak or clear hemolysis which appears to be due to the secretion of $H_2O_2$. This $H_2O_2$ secretion is believed to be responsible for some aspects of the mycoplasmas' pathogenicity. Known mycoplasmas are commonly sensitive to chloramphenicol and tetracyclines.

The *Mycoplasma* genus currently consists of more than 60 known species which are differentiated on the basis of various tests, including utilization of glucose and mannose, arginine hydrolysis, phosphatase production, the "film and spots" reaction and haemadsorption.

Mycoplasmas are the smallest and simplest free-living organisms known. Mycoplasmas are not obligatory intracellular microorganisms and are usually found extracellularly, but can be found intracellularly in the infected tissues (*Mycoplasma*, Eds. Wolfgang, J. J., Willette, H. P., Amos, D. B., Wilfert, C. M., *Zinsser Microbiology* 19th Ed. 1988, Appleton and Lange, 617–623). The term mycoplasma apparently was first used by B. Frank in 1889 (Frank B., *Dent, Bot. Ges.*, 7, 332 (1889) and Krass, C. J. et al., *Int. J. Syst. Bacteriol.* 23, 62 (1973)). Frank, after careful microscopic observation, began writing about invasion of plants (legume) by these microorganisms and stated: "the changed character of the protoplasm in the cortical cells arising from infection, I will designate as mycoplasma". Later, he had more explicitly defined mycoplasma as a mixture of small fungus-like microorganisms and cell protoplasm (Frank, B., *Landwirt. Jahrb.* 19 523 (1890)). The description reflected the difficulty of differentiating this unique microorganism from the infected host cells morphologically.

Even today with electron microscopy, it is still often difficult to differentiate the mycoplasmas from the cellular protoplasmic processes or the subcellular organelles of the infected host, because ultrastructurally, these microorganisms have protoplasm-like internal structures and are bounded by only an outer limited membrane (unit membrane) without a cell wall. Thus, there have been few electron microscopic studies of mycoplasmas identified directly in the infected tissues of animals or humans.

It has been reported that ultrastructural examination of infected tissues has failed to localize the microbe, even in tissues where very high titers (>$10^9$/gm) of microorganisms were recovered in culture (Elizan, T. S. et al., *Pro. Soc. Exp. Biol. Med.* 139, 52 (1972) and Schwartz, J. et al., *Pro. Soc. Exp. Biol. Med.* 139, 56 (1972)). Therefore, morphologically, the microbe might be mimicking certain normal cellular or subcellular structures in the infected host tissues and preventing direct identification.

In addition to the natural difficulty of morphological differentiation between the microorganisms and the protoplasm of infected cells, the often poorly preserved formalin-fixed clinical materials present further limitations to any attempt to directly visualize mycoplasma organisms in the tissues.

Mycoplasmas cause a variety of diseases in animals, plants and insects. However, the roles of known human mycoplasmas except for *M. pneumoniae* in causing a typical pneumonia are difficult to assess. Urines or urogenital swabs from healthy people and patients with a variety of different diseases have already been examined extensively. *U. urealvticum* and *M. hominis* were the most commonly found mycoplasmas. Taylor-Robinson, D., et al., *Nature* 222, 274 (1969); Tarr, P. I., et al., *J. Infec. Dis* 133, 419 (1976); Taylor-Robinson, D., et al., *N. Eng. J. Med.* 302, 1003 (1980); Fiacco, V., et al., *J. Clin. Microbiol.* 20, 862 (1984). Although a wide variety of urogenital and reproductive disorders have been associated with urealyticum and *M. hominis,* it has been difficult to establish a definite etiological role for them because they are often found as frequently in patients without disease as in those with disease. Taylor-Robinson, D., et al., *N. Eng, J. Med.* 302, 1003 (1980). *M. genitalium* was also isolated from two patients with non-gonococcal urethritis. However, most patients with urogenital diseases do not have clear evidence of *M. genitalium* infection. Tully, J. G., et al., *Lancet* 1, 1288 (1981). On the other hand, mycoplasmas are known to be extraordinary pathogens, capable of causing chronic debilitating diseases and producing a variety of clinical manifestations in animals and frequently suppressing host immune defense mechanisms. *The Mycoplasmas,* Vol. IV, Razin, S., Barile, M. F., eds., Academic Press, pp. 203–286 (1983).

Recent studies suggest mycoplasmas may play an important role in the disease progression of AIDS. Lo, S-C., et al., *Am. J, Trop. Med. Hyg.* 40, 213 (1989); Lo, S-C., et al., *Am. J. Trop. Med. Hyg.* 41, 601 (1989), Montagneir, L., et al., *C.R. Acad. Sci. Paris* 311, 425 (1990); Chowdhury, M. I. H., et al., *Lancet* 336, 247 (1990); Bauer, F. A., et al., *Hum. Pathol.* 22, 63 (1991); "Mycoplasma and AIDS—what connection?" [editorial], *Lancet* 337, 20 (1991); Lo, S-C., et al., *Science* 251, 1074 (1991). For example, *Mycoplasma fermentans* systematically infects many patients with acquired immunodeficiency syndrome (AIDS), appears to be associated with diseased conditions in various organs and tissues, and was recently associated with development of nephropathy in AIDS patients. Lo, S-C., et al., *Am. J. Trop. Med. Hyg.* 40, 213 (1989); Lo, S-C., et al., *Am J, Trop. Med. Hyg.* 41, 601 (1989); Bauer, F. A., et al., *Hum. Pathol.* 22, 63 (1991). Examination of polymerase chain reactions and cultures of urines revealed a high prevalence of *M. fermentans* infection in AIDS patients but not in non-AIDS controls.

Description of the Background Art

Acquired Immune Deficiency Syndrome (AIDS) is a devastating disease that has afflicted over one million people worldwide (AIDS Weekly Surveillance Report—United States, Centers for Disease Control, Aug. 29, 1988). The disease is clinically characterized by a set of typical syndromes which manifests itself by the development of opportunistic infections such as pneumocystic carinii pneumonia (PCP), toxoplasmosis, atypical mycobacteriosis and cytomegalovirus (CMV). Further characteristics of the AIDS associated syndromes are the clinical manifestation of neuropsychiatric abnormalities, of AIDS encephalopathy (Naura, B. A., et al., *Ann. Neuro* 19, 517 (1986)), kidney failure of AIDS nephropathy, heart failure of AIDS cardiomyopathy infections and certain uncommon malignancies such as Kaposi's sarcoma or B-cell lymphoma (Durack, D. T., *N. Eng. J. Med,* 305, 1465 (1981); Reichert, C. M., et al., *Am. J. Path.* 112, 357 (1983); Ziegler, J. L., et al., *N. Eng. J. Med.* 311, 565 (1984)).

Through co-cultivation of AIDS patients' peripheral blood cells with mitogen-stimulated normal human lymphocytes or permanent human T-cell lines, a number of laboratories have isolated T-cell-tropic human retroviruses (HIV), Barre-Sinoussi, F., et al., *Science* 220, 868 (1983); Gallo, R. C., et al., *Science* 224, 500 (1984). Epidemiologically, the newly isolated retroviruses have been shown to be highly associated with patients of AIDS and/or AIDS-related complex (ARC). Schupback, J., et al., *Science* 224, 503 (1984); Sarngadharan, M. G., et al., *Science* 224, 506 (1984). In vitro studies with HIV have demonstrated T-cell tropism and cytopathic changes. Barre-Sinoussi, F., et al., *supra;* Popovic, M., et al., *Science* 224, 497 (1984). HIV is believed to be the causative agent of AIDS.

However, the establishment of an animal model of AIDS by HTLV-III-LAV injection has not been successful. Gajdusek, D.C., et al., *Lancet I,* 1415 (1984). The chimpanzee is the only primate other than man found to be susceptible to infection by HIV. However, overt AIDS manifested by the development of opportunistic infections and/or unusual malignancies has not yet been seen, despite evidence for persistent infection and/or viremia in experiments on this species. Gajdusek, D.C., et al. *Lancet I,* 55 (1985). Thus, the human retroviruses have not fulfilled Koch's postulates, i.e., producing transmissible AIDS-like diseases in experimental animals. HIV is not associated with the unusual malignancies such as B-cell lymphoma and Kaposi's sarcoma, commonly found in patients with AIDS. Shaw, G. M., et al., *Science* 226, 1165 (1984); Delli Bovi, P., et al., *Cancer Research,* 46, 6333 (1986); Groopman, J. E., et al., *Blood* 67, 612 (1986). Furthermore, HIV infected patients often show a wide variation in times of disease incubation and speed of disease progression. It is not known whether any specific infectious agent other than HIV can be responsible for the complex pathogenesis often seen in this disease. One such candidate, initially identified as a virus or virus-like infectious agent is *M. fermentans* (incognitus strain). See, Lo, S-C., et al., *Am. J. Trop. Med. Hyg.* 40, 213 (1989); Lo, S-C., et al., *Am. J. Trop. Med. Hyg.* 41, 601 (1989).

The recognition of the incognitus strain of *M. fermentans* as a possible causative or opportunistic agent associated with AIDS has instigated the search for other pathogenic mycoplasmas which may contribute to a better understanding, diagnosis, prognosis, and treatment of AIDS.

SUMMARY OF THE INVENTION

The present invention relates to a novel mycoplasma which has been isolated from the urine of HIV[+] patients with AIDS. This mycoplasma has been tentatively designated as *Mycoplasma penetrans.*

This novel mycoplasma is structurally characterized by two sharply divided compartments which are easily distinguished both externally and internally. The novel mycoplasma also possesses the pathobiological properties of adhesion, hemadsorption, cytadsorption and invasion into mammalian cells. Furthermore, the novel mycoplasma utilizes both glucose and arginine for growth. Antigenic and DNA analyses reveal that the mycoplasma is previously unknown.

The invention also relates to the use of this mycoplasma, *M. penetrans,* and similar mycoplasmas with homologous antigenic determinants for the detection of specific antibodies in the sera of human patients and animals, and for vaccines against mycoplasmas. The invention further relates to antibodies, including monoclonal antibodies, to *M. pen-*

*etrans* and to homologous antigenic determinants of *M. penetrans* antigens in the infected tissue of human patients and animals. The invention still further relates to sequencing the DNA of *M. penetrans* and the manufacture of DNA probes based on such sequencing and homologous sequences of *M. penetrans* for use in the direct detection of the unique DNA sequences in the tissues of human patients and animals.

The invention also relates to the detection of the presence of *M. penetrans* in patients who are HIV-positive or have other sub-acute or acute fulminant systemic disease as an indication of the prognosis of the disease, which can be used to determine the appropriate therapy regimen.

BRIEF DESCRIPTION OF THE DRAWINGS

The various aspects, advantages, and novel features of the present invention will be more clearly understood from the following detailed description when read in conjunction with the appended figures, in which:

In FIG. 3A, the blot was probed with $^{32}$P nick translated genomic DNA of *M. penetrans*. The concentrations of total DNA isolated from various mycoplasmas were dot-blotted incrementally from lane 1 (2 ng), lane 2 (20 ng) to lane 3 (200 ng). Row a shows *M. penetrans*; b, *M. fermentans* (incognitus strain); c, *M. fermentans* (PG18 strain); d, *M. pirum*; e, *M. pneumoniae*; f, *M. genitalium*; g, *M. hominis*; h, *U. urealyticum*; i, *M. orale*; j, *A. laidlawii*; k, *M. salivarium*; and l, *M. buccale*: m, n, o, p, contain the DNA from four of the six isolates cultured from the urines of this HIV$^+$ AIDS patient in the subsequent six isolation attempts.

In FIG. 3B, the Southern blots were probed with $^{32}$P-labeled insert DNAs from clones M6A1-3.2 (I), M6A1-3.1 (II) and M6A1-2.9 (III), and $^{32}$P-labeled cDNA probe of *E. coli* ribosomal RNA (IV). Lanes contained 0.2 ug EcoRI enzyme pre-digested DNA from *M. pneumoniae* (lane a), *M. genitalium* (lane b), *M. fermentans* (incognitus strain) (lane c), *M. fermentans* (PG18 strain) (lane d), *M. pirum* (lane e), *M. iowae* (lane f), *M. alvi* (lane g), *M. moatsii* (lane h), *M. sualvi* (lane 1) and *M. penetrans* (lane j). Arrows indicate the positions of standard size markers from top to bottom, 21.7, 5.08, 4.27, 3.46, 1.94, 1.59, 1.37, 0.94, and 0.83 kb, respectively.

Specifically, FIG. 4A shows adhesion of *M. penetrans* on the surface of plastic culture flasks. The organisms cultured in SP-4 broth aggregate into different sizes of microspherules and adhere to the flask surface.

FIG. 4B shows massive cell aggregation induced by *M. penetrans*. Introduction of $10^7$ CFU *M. penetrans* into 25 ml suspension of U937 human monocytes culture ($10^6$ cells/ml) produces prominent cell-cell aggregation in 24 hours. Only occasional unaggregated cells (arrows) are identified.

FIG. 4C shows hemadsorption of *M. penetrans*. Human RBC prepared from type O, Rh$^-$ healthy donor are firmly adsorbed on the *M. penetrans* fried egg colonies (c) of various sizes on agar plate. The unadsorbed RBC were washed out from the plate.

FIGS. 4D and E show cytadsorption of *M. penetrans*. Human monocyte U937 cells (D) and human $CD_4^+$ CEM lymphocytes (E) are firmly adsorbed on *M. penetrans* colonies (c) on the agar plate, after 30 minutes incubation at 37° C.

FIG. 4F shows that *M. hominis* has no cytadsorption property. Even after only a mild wash, none of the $CD_4^+$ human lymphocytes (CEM) (arrows) appear to be associated with *M. hominis* colonies (c).

Specifically, FIG. 5A shows a monolayer culture of Vero cells with a flat cobble stone feature.

FIG. 5B shows the same culture with profound cytopathic changes after 48 hours of *M. penetrans* infection ($10^8$ CFU in 75 cm$^2$ culture). Degeneration and cell death associated with production of granular materials are readily identified after 24 hours of infection.

Specifically, FIG. 6A shows numerous organisms adhering on the surface of a normal human umbilical cord endothelial cell leaving the surrounding cells (*) unaffected. Nucleus (N) and mitochondria (m) of the infected cell are unremarkable. Microvilli (V) of the endothelial cells are identified. The bar represents 500 nm.

FIG. 6B shows FIG. 6A at higher magnification and reveals many organisms lining along the cell surface with their tip-like structures of densely packed fine granule compartment (F) inserted into the cell while the body compartment of loosely packed coarse granules (C) remained outside. The insert shows the active invasion process at even higher power. Both the deeply invaginated cytoplastic membrane (arrowheads) and the organism's membrane (arrow) are identified. The bars represent 100 nm.

FIG. 6C shows an endothelial cell with numerous organisms already invaded into the cytoplasm. Most of the intracellular organisms are in clusters inside membrane bound vacuoles (arrows). Nucleus (N) and mitochondria (m) of this cell remain unremarkable. A surrounding cell (*) with surface-associated organisms (curved arrow) is also noted. The bar represents 1000 nm. The insert reveals the intracellular mycoplasmas located within a membrane bound vesicle (arrowheads) at a higher power. Distinct components of the fine granules (F) and the coarse granules (C), as well as the external unit membrane (arrows) of organisms can be identified. In the insert, the bar represents 100 nm.

FIG. 6D shows cell death is induced by extensive invasion of *M. penstrans*. Many organisms are in cytoplasmic vacuoles (arrows). Others actively invade the cell and apparently cause complete disruption of the cell (curved arrow). The degenerating nucleus (N) is identified. The bar represents 1000 nm.

Specifically, FIG. 7A shows *M. penetrans* adhering (curved arrow) to the cell surface and piercing their tip compartments into the cytoplasm (Cy) of a urogenital epithelial cell with microvilli structure (V). The insert shows the same adhesion and invasion processes at higher magnification. The invaginated cytoplasmic membrane of the epithelial cell (arrowheads) is still well preserved. The sharply divided compartments of fine granules (F) and coarse granules (C), and the trilaminar membrane (arrow) of *M. penetrans* can be clearly identified. The bar represents 100 nm.

FIG. 7B shows a urothelial cell with both surface associated *M. penetrans* (curved arrows) and intracellular organisms in membrane bound vacuoles (arrows). Mitochondria (m), microvilli (v) and microridges of the urothelial cell are noted. The bar represents 400 nm. The insert reveals the intracellular organisms in cytoplasmic vacuoles (arrowheads). The unit membrane of these organisms is also identified (arrows). The bar in the insert represents 100 nm.

DETAILED DESCRIPTION OF THE INVENTION

The present invention relates to a novel mycoplasma, tentatively designated *M. penetrans* which is found in patients with AIDS. *M. penetrans* has been isolated repeatedly in high titers from the urine of HIV+ patients with AIDS.

Figure 1A:
FIG. 1A is an electron photomicrograph of *M. penetrans*. The *M. penetrans* cells were grown in SP-4 broth culture, spread on foamvar coated grids directly, and stained by phosphotungstic acid (2%, pH 7.2). The arrows indicate the more densely packed tip structure of the microorganism, and the open arrows indicate the broader body compartment. The insert to FIG. 1A reveals the two distinct compartments plus unit membrane (arrow heads). The bars represent 400 nm (FIG. 1A) and 100 nm (insert).
Figure 1B:
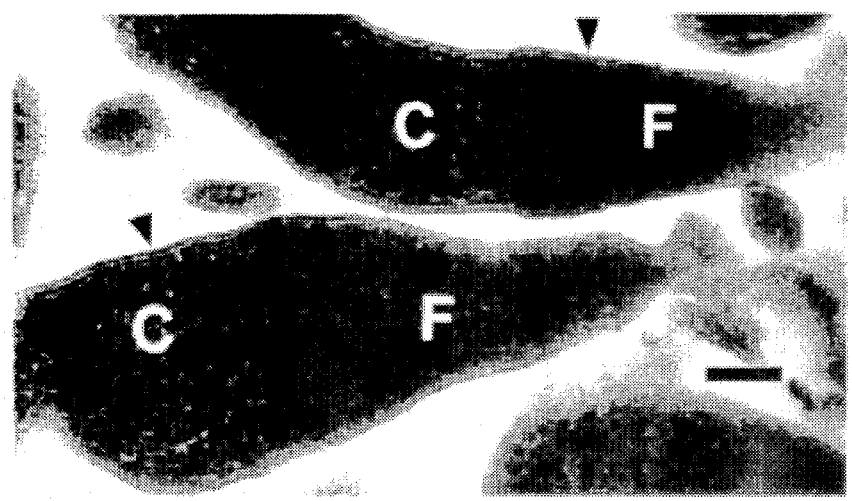
FIG. 1B is an electron photomicrograph of an ultra-thin sectioned pleomorphic *M. penetrans*. The tip-like structure at the narrowing end contains densely packed very fine granules (F) and the broader compartment or the body of organisms contains loosely packed coarse granules (C). Organisms have a single trilaminar unit membrane (arrow heads) without a cell wall. The bar represents 100 nm.

One of the unique physical characteristics of *M. penetrans* is its ultrastructure which consists of two sharply divided compartments which are easily distinguished both externally and internally. The two compartments are: (1) a densely packed tip-like structure; and (2) a more loosely packed body. These ultrastructional features are best shown in FIG. 1A. The tip-like structure is designated by the arrows in FIG. 1A, and the broader body compartment is designated by the open arrows. The insert to FIG. 1A shows the unit membrane between these two morphologic features of *M. penetrans*. As shown in FIG. 1B, electron microscopy of ultra-thin sectioned organisms also revealed two sharply divided compartments internally, bound only by a single triple layered unit membrane.

Figure 2:
FIG. 2 is an electron photomicrograph of *M. penetrans* cells lining the surface of an infected human endothelial cell with tip-like structures of densely packed fine granules (F) deeply inserted into the cytoplasm and the body compartment of loosely packed coarse granules (C) remaining outside. The deeply invaginated membrane (arrows) and microvilli (V) of the endothelial cells are identified. One organism (curved arrow) has completely penetrated into the cell and is seen intracellularly. The bar represents 100 nm.

As stated above, the compartment forming the tip-like structure is densely packed with very fine granules designated "F" in FIGS. 1B and 2. In contrast, the broader compartment of *M. penetrans* was filled with loosely packed coarse granules consistent with ribasomal structures. These coarse granules are designated "C" in FIGS. 1B and 2. The culturing of *M. penetrans* in antibiotic-free media did not promote cell wall formation.

This unusual compartmental structural has only been found in one other mycoplasma, *M. iowae*. Although *M. iowae* was reported to have fine and coarse granule compartments, it is a pathogenic avian mycoplasma. Mirsalimi, S. M., et al., *Avian Dis.* 33, 310 (1989).

As also shown in FIGS. 1A, 1B and 2, electron microscopy with negative staining revealed that most *M. penetrans* organisms are rod-like in shape. Furthermore, most of the organisms are about 0.2 to 0.4 µm wide and about 0.8 to 2.0 µm long.

The originally isolated *M. penetrans* was triple filtered-cloned as previously described by Lo, S-C., et al. in *Am. J. Trop. Med. Hyg.* 41, 586 (1989). Then, a specific clone (6A1) was used for subsequent biochemical and molecular biological characterization.

The mol % G+C of the *M. penetrans* 6A1 clone DNA was determined to be 30.5 by studying Tm for hyperchromatic shift as previously described by Marmur, J., et al. in *J. Mol. Biol.* 5, 109 (1962). This low G+C content is a typical characteristic of mycoplasmal DNA.

*M. penetrans* was found to oxidize/ferment glucose, and also positively displayed arginine deiminase enzyme activity utilizing the techniques of Barile, M. F., *Methods in Mycoplasmology*, Vol. I, Razin, S. and Tully, J. G. eds., pp. 345–349 (1983) and Aluotto, B. B., et al., *Intl. J. Sys. Bacteriol.* 20, 35 (1970). Human mycoplasmas, *M. fermentans* and *M. pirum*, and animal mycoplasmas, *M. alvi*, *M. sualvi*, *M. moatsii* and *M. iowae* are the mycoplasmas previously known to utilize both glucose and arginine for growth. Both antigenic and DNA analyses reveal that *M. penetrans* is distinct from all these species of mycoplasma. The biological and biochemical properties of *M. penetrans* are summarized in Table 1, below.

TABLE 1

| Biological and Biochemical Characteristics of *M. penetrans* | |
|---|---|
| Properties | Results |
| Formation of "fried egg" colonies | + |
| Glucose fermentation/oxidation | + |
| Arginine hydrolysis | + |
| Urea hydrolysis | − |
| Cholesterol requirement | + |
| Digitonine sensitivity | + |
| Phosphatase activity (aerobic/anaerobic)[a] | + |
| Tetrazolium chloride reduction (aerobic/anaerobic)[b] | + |
| Film and spots formation | − |
| Adhesion to glass or plastic surface | + |
| Hemadsorption | + |
| Cytadsorption | + |
| Hemolysis | |
| Alpha hemolysis | weak |
| Beta hemolysis | − |
| G + C content of DNA | 30.5% |

[a]. Bradbury, J. M., Methods in Mycoplasmology, Vol. I, Academic Press, Razin, S., Tully, J. G. eds., p. 363 (1983).
[b]. Senterfit, L. B., in Ref. Methods in Mycoplasmology, Vol. I, Academic Press, Razin, S., Tully, J. G. eds., p. 377 (1983).

Figure 4:
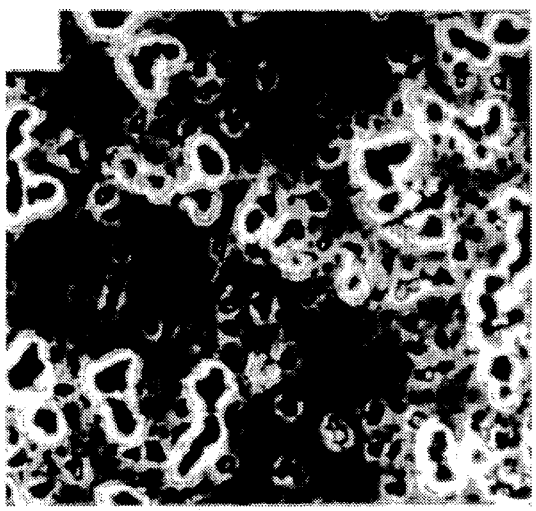
FIGS. 4A, 4B, 4C, 4D, 4E and 4F illustrate in vitro pathobiological properties of *M. penetrans*.
Figure 4:
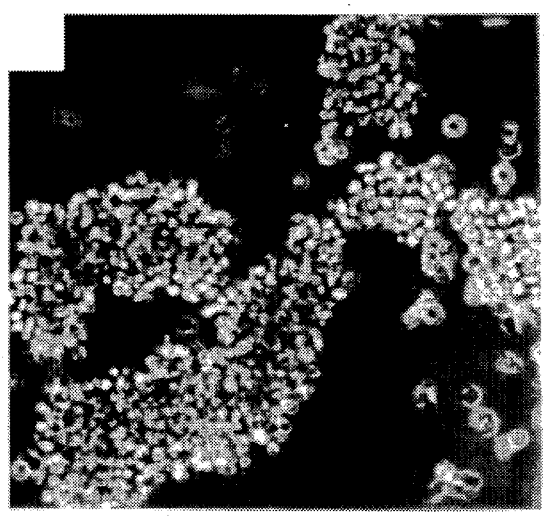

Some of the biochemical properties summarized in Table 1 are also uniquely illustrated in FIG. 4. Particularly, FIG.

4A illustrates the adhesion of *M. penetrans* on the surface of a plastic culture flask as aggregates of microspherules.

Similarly, FIG. 4B shows the massive cell-cell aggregation of U937 human monocytes only 24 hours after introduction of *M. penetrans*. Only occasional unaggregated cells are identified by the arrows.

Figure 4C:
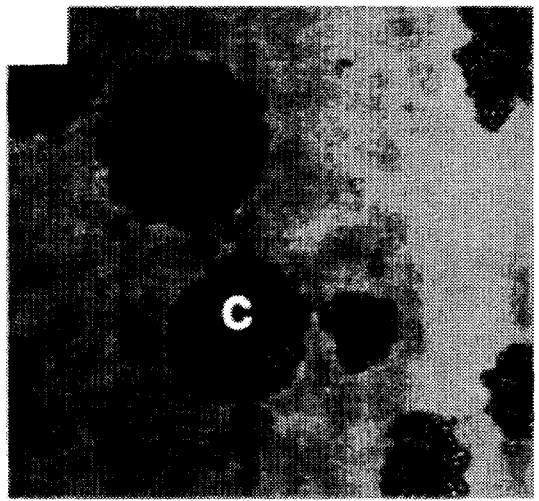
Figure 4:
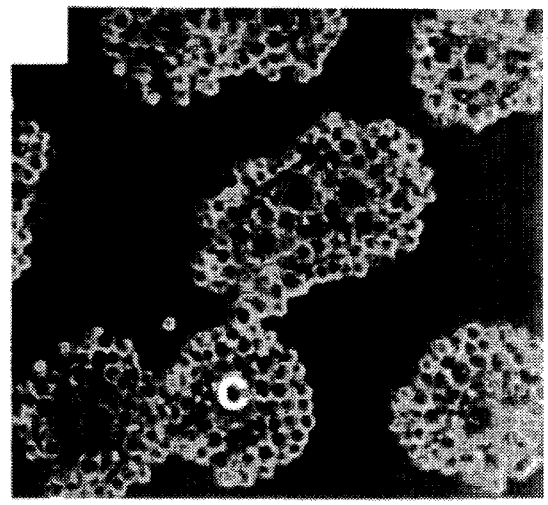
Figure 4E:
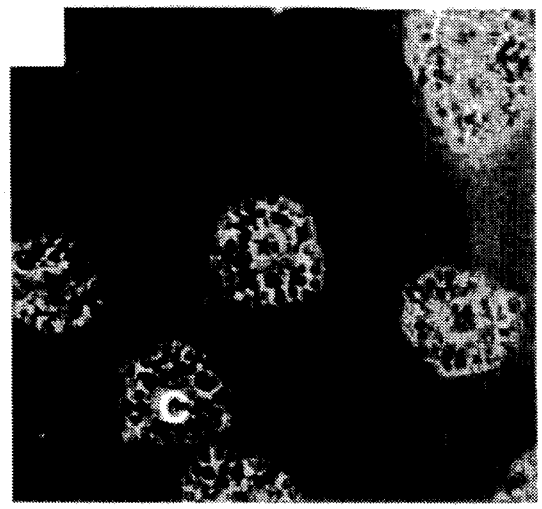
Figure 4:
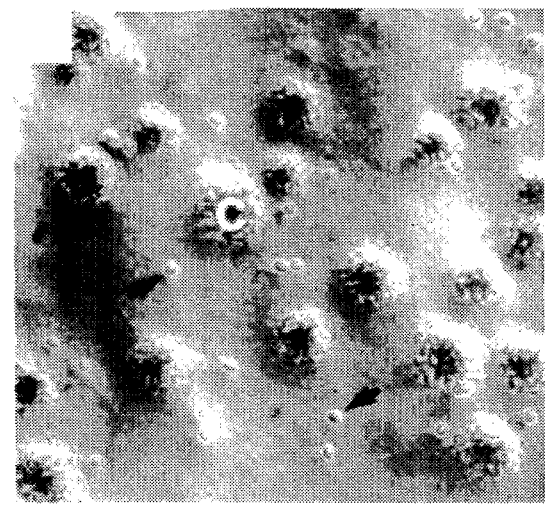

The hemadsorption property of *M. penetrans* is illustrated in FIG. 4C which shows human red blood cells adsorbed on the "fried egg" colonies (c) of *M. penetrans*. The unadsorbed red blood cells were washed from the plate.

FIGS. 4D and E show the cytadsorption of human monocyte U937 cells (4D) and human $CD^+_4$ CEM lymphocytes (4E) to *M. penetrans* (c) on an agar plate. In contrast, FIG. 4F shows that human $CD^+_4$ CEM lymphocytes (arrows) do not associate with *M. hominis* colonies (c).

In cell cultures, attachment on the surface of human or animal cells was followed by active invasion of the adherent *M. penetrans*. The tip-like structures with densely packed fine granules act as "spearheads". FIG. 2 reveals spearheads deeply buried in a normal human umbilical cord endothelial cell. The entire organisms completely penetrated into the cytoplasm and caused a varying degree of cytopathic effects of the infected cells. Active invasion by *M. penetrans* was similarly observed in cultures of human embryonal kidney cells, cervical carcinoma cells (Hela), $CD_4^+$ lymphocytes (CEM), human monocytic cells (U937), monkey kidney cells (Vero) and NIH/3T3 cells.

The invasive process of *M. penetrans* is well illustrated in FIGS. 5, 6 and 7. Particularly, FIG. 5 shows the cytopathic effects of *M. penetrans* infection of Vero cells.

Figure 5A:
FIGS. 5A and 5B illustrate cytopathic effects produced by *M. penetrans* infection.
Figure 5B:

FIG. 5A is a monolayer culture of Vero cells with a characteristic flat cobble stone appearance. However, the same culture is shown in FIG. 5B after 48 hours of *M. penetrans* infection at $10^8$ CFU in 75 $cm^2$ of culture. Degeneration and cell death associated with the production of granular materials was already identified only 24 hours after infection.

Similarly, FIG. 6 illustrates *M. penetrans* adhesion and invasion of mammalian cells. Specifically, FIG. 6A shows *M. penetrans* adhering to the surface of normal human umbilical cord endothelial cells, with the nucleus (N) and mitochondria (m) of the infected cells being unremarkable. FIG. 6B shows FIG. 6A at a higher magnification so that the insertion of the *M. penetrans* tip-like structure into the infected cell can be seen. The insert to FIG. 6B is an even higher magnification of the same invasive process.

Figure 6A:
FIGS. 6A, 6B, 6C and 6D illustrate adhesion and invasion of mammalian cells by *M. penetrans*.
Figure 6B:
Figure 6C:
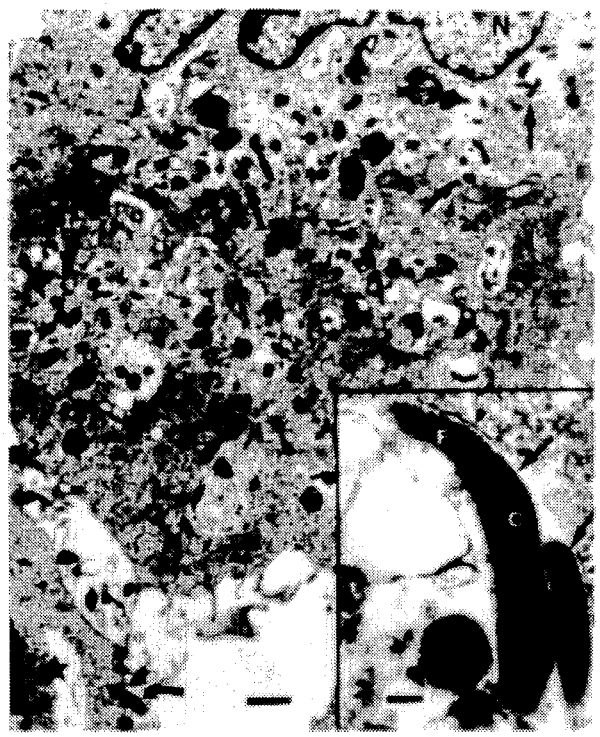
Figure 6D:
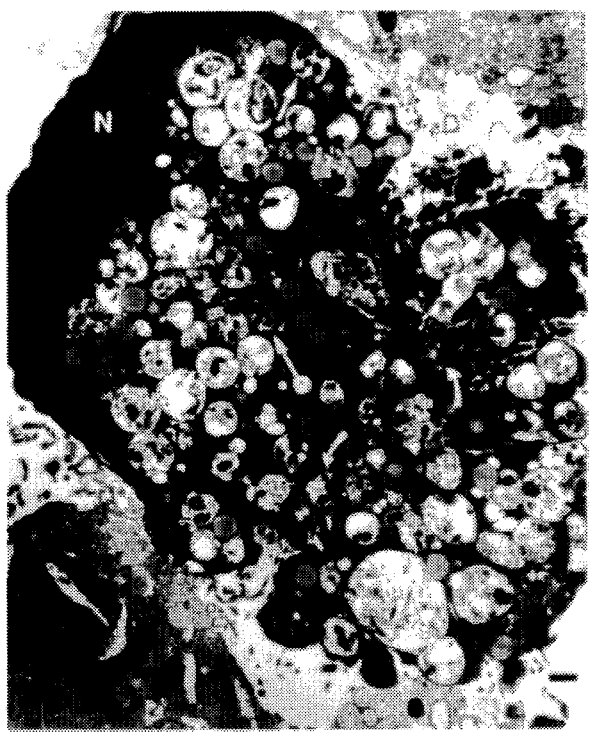

FIGS. 6C and D show further progress of the invasive process. Particularly, FIG. 6C shows numerous *M. penetrans* organisms already invading into the cytoplasm of the endothelial cells, with most of the intracellular organisms in clusters inside membrane bound vacuoles (arrows). However, the nucleus (N) and mitochondria (m) still remain unremarkable. Finally, FIG. 6D illustrates cell death induced by extensive invasion of *M. penetrans*. Complete disruption of the cell is shown by the curved arrow, and the degenerating nucleus (N) is also identified.

Figure 7B:
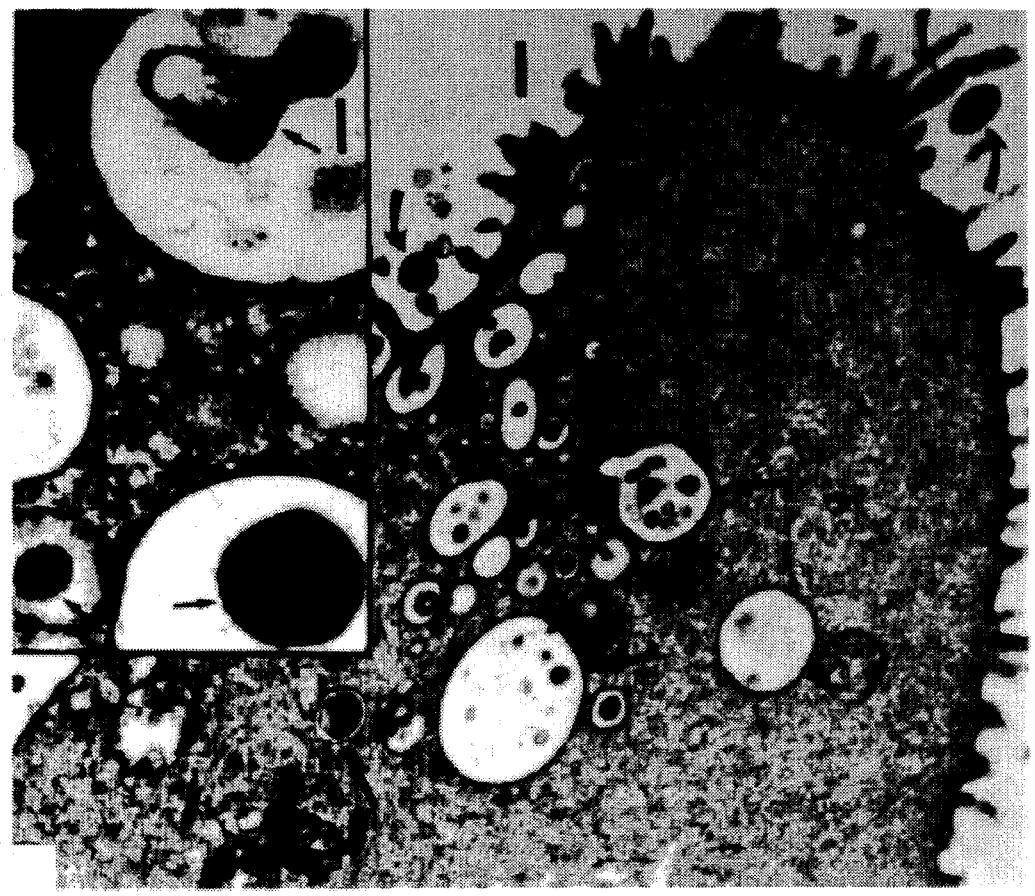
FIGS. 7A and 7B identify *M. penetrans* infection in a patient's urothelium.
Figure 7A:
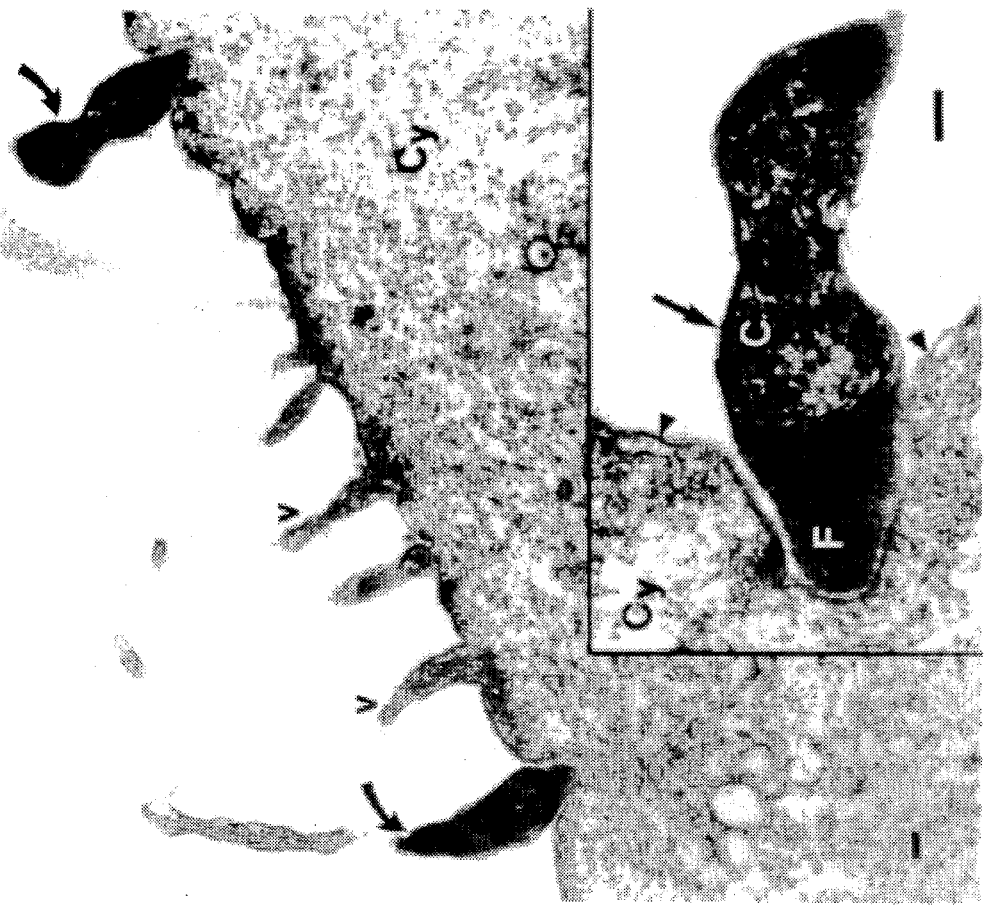

*M. penetrans* infection of human urothelium cells is shown in FIG. 7. Specifically, FIG. 7A shows the initial stages of the infection in which *M. penetrans* adheres to the cell surface (curved arrow) and inserts its tip-like structure into the cytoplasm (Cy) of the cell. The insert to FIG. 7A shows the invasive process at a higher magnification, and confirms that the cytoplasmic membrane of the urogenital epithelial cell is still well preserved as designated by the arrowheads.

However, FIG. 7B shows the invasive process at a further stage where there are both surface associated *M. penetrans* organisms (curved arrows) and intracellular *M. penetrans* organisms (arrows). The insert to FIG. 7B shows the intracellular *M. penetrans* in cytoplasmic vacuoles as designated by the arrowheads.

*M. penetrans* is antigenically different from any of the other human or animal mycoplasmas. Polyclonal rabbit antibody raised against each of the human mycoplasmas, *M. fermentans* (incognitus strain and PG-18), *M. pirum, M. pneumoniae, M. genitalium, M. orale, M. salivarium, M. hominis* or *Acholeplasma laidlarvii* did not react with *M. penetrans* in dot-blot immunochemical assay or an immunofluorescence assay (data not shown). Conversely, rabbit antiserum raised against *M. penetrans* failed to react with these mycoplasmas in the assays.

Figure 3A:
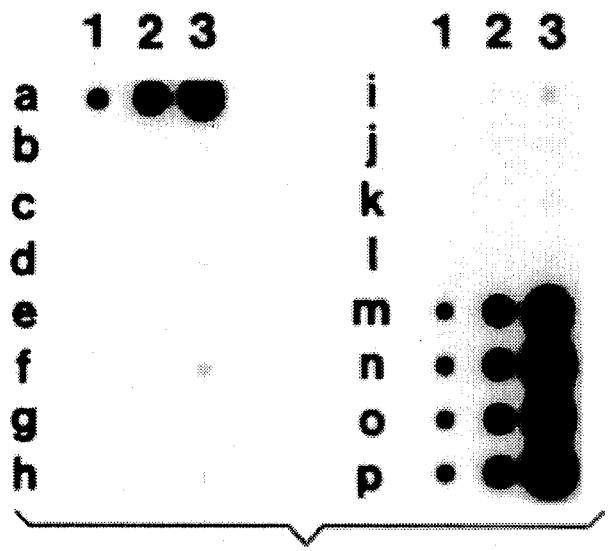
FIGS. 3A and 3B show a comparison of DNA homology between *M. penetrans* and other human mycoplasmas or the mycoplasmas with similar unusual biochemical properties.
Figure 3B:
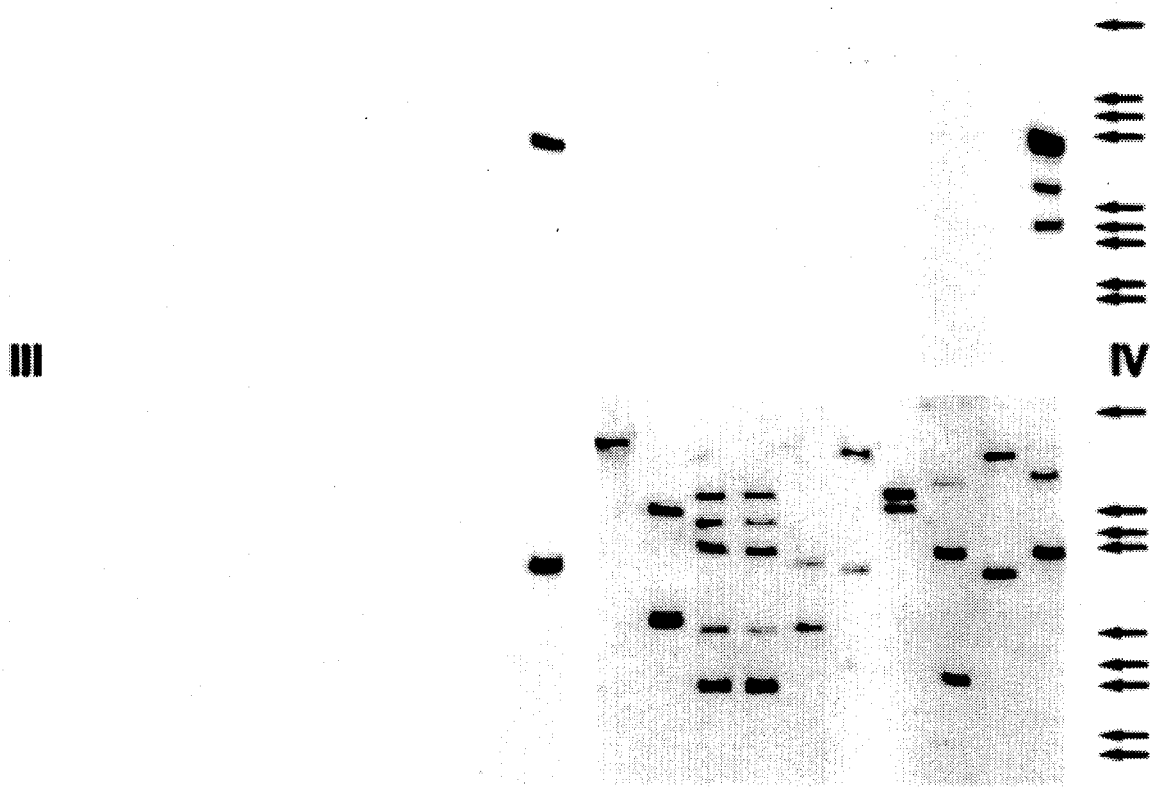

$^{32}$P-labeled genomic DNA from *M. penetrans* clone 6A1 was used as a probe and hybridized with DNA from other human mycoplasmas and animal mycoplasmas known to utilize both glucose and arginine. There was no significant DNA homology (FIG. 3A). The same mycoplasma (*M. penetrans*) has been isolated from urines of the initial patient in each of the subsequent six isolation attempts. The identity of all 6 subsequent isolates was confirmed by the morphological, biochemical, antigenic and DNA analyses (FIG. 3A, lanes m,n,o,p). Southern blot analysis using $^{32}$P-labeled recombinant DNAs (M6A1-3.2, M6A1-3.1 and M6A1-2.9) molecularly cloned from the 6A1 clone of *M. penetrans* as probes also revealed a lack of homology between *M. penetrans* and other species of human mycoplasmas and animal mycoplasmas with the same biochemical properties (FIG. 3B).

The characteristic restriction enzyme mappings of r-RNA genes in the mycoplasma group often enable the identification of related species. The EcoRI restriction pattern of r-RNA genes for *M. penetrans* was different from any of those mycoplasmas tested (FIG. 3B-IV).

In addition to the original isolate of *M. penetrans*, successful isolation of the new mycoplasma from urines of five additional HIV$^+$ patients with AIDS has been accomplished. These urine samples were part of those obtained from 75 HIV$^+$ patients submitted from a second AIDS clinic. Ultrastructural, biochemical, antigenic and DNA studies revealed the 5 additional isolates share the same properties as the original *M. penetrans* isolate. For the present study, urines from 98 young, HIV$^-$ persons were cultured in parallel as controls, and no organisms similar to *M. penetrans* were identified.

The *M. penetrans* properties of cell adhesion and cytoplasm invasion remain actively stable in human, monkey or mouse cell cultures, and in cells of epithelial, endothelial, fibroblastic, lymphocytic and monocytic lineages. Electron micrographic studies of *M. penetrans* invading cells reveals the definite orientation of the organism. Using its specific ultrastructure, *M. penetrans* is capable of penetrating a variety of different types of mammalian cells from various species, some with minimal pinocytic or phagocytic ability. This is most likely an active property of this unique organism without requiring a restricted receptor(s) on the surface of the cells infected.

The entire pathobiological properties of adhesion, hemadsorption, cytadsorption and active invasion of *M. penetrans* appear to involve its specialized tip-like structure. The attachment and invasion structure of *M. penetrans*, reminiscent of those observed with *M. pneumoniae, M. genitalium* and *M. gallisepticum*, is however ultrastructurally unique. The distinct morphology of *M. penetrans* with two completely separated compartments can readily be recognized both internally and externally. The nature of these structures is not clear at the present time.

In previous studies of human or animal mycoplasmas, adhesion, hemadsorption and cytadsorption are the best characterized pathobiological properties associated with the virulence or pathogenicity of mycoplasmas. Chandler, D. K. F., et al., *Infect. Immun.* 38, 604 (1982); Barile, M. F., et al., *Infect. Immun.* 56, 2443 (1988). However, the characteristic of active penetration or invasion into mammlian cells found in *M. penetrans* is highly unusual. Mollicutes are generally considered to be extracellular organisms and not to actively invade mammalian cells. Preliminary study reveals that extensive invasion of the *M. penetrans* into cytoplasm of the infected cells can produce profound cytopathic effects and lead to cell death in cell cultures. In this context, it is important to note *M. penetrans* apparently uses the same mechanism, involving its specialized tip-like structure, to adhere onto and invade into urothelial cells in the patient's urogenital tract (see FIG. 7).

This unique mycoplasma, *M. penetrans*, was deposited with the American Type Culture Collection 12301 Parklawn Drive, Rockville, Md. 20852, USA on Nov. 19, 1991, and is assigned ATCC Designation 55252.

Furthermore, as mentioned above, *M. penetrans* DNA has been molecularly cloned and designated M6A1-2.9, M6A1-3.1 and M6A1-3.2. Of these clones, M6A1-2.9 and M6A1-3.2 have been partially sequenced. The partial sequence of M6A1-2.9 is designated SEQ ID NO:1, and the partial sequence of M6A1-3.2 is designated SEQ ID NO:2. SEQ ID NO:1 is a 276 base pair fragment and SEQ ID NO:2 is a 308 base pair fragment.

Conventional methodology is used to recover *M. penetrans* DNA from human or animal samples or culture samples. First, the mycoplasma is treated with a proteinase such as Proteinase K. Genetic materials are obtained after phenol extraction, phenol/chloroform/isoamylalcohol extraction, and chloroform/isoamylalcohol extraction. High molecular weight DNA is visibly observed after ethanol precipitation of the genetic materials. The genetic materials are dissolved and contain high molecular weight DNA and RNA of various sizes.

Mycoplasma DNAs are extremely rich in A and T. It has already been shown in the codon usage of ribosomal protein genes of *M. capricolum* that synonymous nucleotide substitution and conservative amino acid substitution can occur (Muto et al., *Nucleic Acids Res.,* 12 8209 (1984)). It has also been reported that TGA, instead of being a stop codon, is a Trp codon in many species of mycoplasma (Yamao et al., *Proc. Natl. Acad. Sci. USA,* 82 2306 (1985)); Inamine et al., *J. Bacteriol.,* 172 504 (1990)).

The *M. penetrans* pathogen is useful for the detection of antibodies in the sera of patients or animals infected with *M. penetrans.* Some of these patients who are infected with *M. penetrans* can possibly be patients who have been diagnosed as having HIV infection, AIDS or ARC, Chronic Fatigue Syndrome, Wegener's Disease, sarcoidosis, respiratory distress syndrome, Kibuchi's disease, antoimmune diseases such as collagen vascular disease and lupus and chronic debilitating diseases such as Alzheimer's Disease. In one procedure, persistently *M. penetrans* infected cells are grown in low cell density on sterile glass slides. Sera from suspected patients, and normal subjects are examined in an immunoperoxidase staining procedure such as that described by Hsu, S-M., et al., *Am. J. Clin. Path.* 80, 21 (1983). Using this assay, sera from AIDS patients will show strong positivity. However, sera from non-AIDS normal subjects will not show reactivity or will show weak reactivity. In addition, some of the sera from experimentally infected animals also contain antibodies which react with the persistently *M. penetrans* infected cells in this assay procedure. Similarly, *M. penetrans* infected cells can also be used in this procedure to detect antibodies in sera of infected patients as a result of homologous antigens.

In addition to this procedure, any other procedure for detecting an antigen-antibody reaction can be utilized to detect antibodies to *M. penetrans* in the sera of AIDS patients or patients with ARC. Such procedures include, but are not limited to, ELISA, Western-blot, direct or indirect immunofluorescent assay and immunoradiometric assay. Such assay procedures for the detection of antibodies in sera of AIDS patients or patients with ARC have been described in U.S. Pat. No. 4,520,113, incorporated herein by reference, which uses HIV as the antigen. Similar procedures employing *M. penetrans* can be used. A diagnostic kit for the detection of *M. penetrans* specific antibodies can be prepared in a conventional manner using *M. penetrans.* It is expected that assays utilizing these techniques, especially Western-blot, will provide better results, particularly, fewer false-positives.

A final procedure for detecting the presence of *M. penetrans* in tissues, blood or body fluids of suspected patients is by testing for DNA in conventional methods, preferably using probes based on *M. penetrans* sequences such as SEQ ID NO:1 and SEQ ID NO:2. One such probe which has been developed from these sequences is SEQ ID NO:3, also referred to as probe RW-012. A preferred method is a polymerase chain reaction (PCR) assay as described in U.S. Pat. No. 4,683,202. When utilizing PCR, the forward primer, RW-010 (SEQ ID NO:4) and reverse primer, RW-011 (SEQ ID NO:5) have been found to be useful.

A PCR assay to detect *M. penetrans* was designed on the basis of specific nucleotide (nt) sequences, SEQ ID NO:1 AND SEQ ID NO:2. Primers (RW-010 (SEQ ID NO:4) and RW-011 (SEQ ID NO:5)) were chosen to produce an amplified DNA fragment of 195 bp. (See Example 9.) The PCR assay detected very specifically the mycoplasmas of *M. penetrans* species but not other human or non-human mycoplasmas, bacteria or eucaryotic cells DNA that were tested.

Specificity of the reaction was examined by attempting to amplify the DNAs isolated from other human or non-human mycoplasmas, common tissue culture contaminating mycoplasmas, Gram-positive or Gram-negative bacteria, mouse, monkey and human cell culture and/or tissue. The reaction does not produce the specific 195 bp DNA fragment.

Antibodies against *M. penetrans* can be produced in experimental animals such as mice, rabbits and goats, using standard techniques. Alternatively, monoclonal antibodies against *M. penetrans* antigens can be prepared in a conventional manner. Homologous antibodies are useful for detecting antigens to *M. penetrans* in infected tissues such as lymph nodes, spleen, Kaposi's sarcoma, lymphoma tissue, brain and peripheral blood cells, as well as sera, urine or body fluids of patients with AIDS. Any procedure useful for detecting an antigen-antibody reaction, such as those described above, can be utilized to detect the *M. penetrans* antigens in specimens from patients infected by the mycoplasma.

Rabbit antiserum can be prepared using *M. penetrans.* The antiserum will positively immune stain *M. penetrans*-infected tissue from AIDS patients. To produce the antiserum, sucrose gradient banded *M. penetrans* or pure cultures of *M. penetrans* are used with complete adjuvant and administered to rabbits by intraperitoneal and subcutaneous injections at multiple sites. Serum collected from the rabbits is then preabsorbed with NIH/3T3 cells, mouse liver powder and normal human peripheral mononuclear cells isolated from Ficoll-Hypaque gradients. Monoclonal antibodies may also be prepared by conventional procedures.

The antibodies are useful for detecting cells which have been infected by *M. penetrans*. This capability is useful for the isolation of *M. penetrans* from other tissues. For example, additional *M. penetrans* can be isolated by co-cultivating infected tissue from patients with AIDS and a suitable recipient cell line or cells, such as lymphocytes. The infected cells are assayed or recognized by the antibody, and *M. penetrans* can be obtained from the infected cells as described above. An affinity column can also be prepared using the antibodies and used to purify the *M. penetrans* from the infected cell lysate.

The *M. penetrans* pathogen, antigens of *M. penetrans* or homologous antigens of *M. penetrans* can be utilized as a vaccine in a conventional manner to induce the formation of protective antibodies or cell-mediated immunity. The antigens can be isolated from *M. penetrans* or can be produced by conventional recombinant DNA techniques. The vaccines are prepared by usual procedures, such as by in vitro cell cultures, by recombinant DNA techniques, and by application of the usual and prescribed controls to eliminate bacterial and/or viral contaminations, according to well known principles and international standard requirements.

Preferably an inactivated, i.e., attenuated or killed, vaccine is utilized. The *M. penetrans* pathogen is isolated from the infected cells grown in monolayers. *M. penetrans* is killed by known procedures or modifications thereof, e.g., by the addition of betapropiolactone, Formalin or acetylethyleneimine, by ultraviolat radiation, or by treatment with psoralen or psoralen derivatives and long-wavelength ultraviolet light. Alternatively, *M. penetrans* is attenuated by conventional techniques and isolated.

The vaccine of the invention may contain one or more suitable stabilizers, preservatives, buffering salts and/or adjuvants. The vaccine may be formulated for oral or parenteral administration. Compositions in the form of an injectable solution contain a proper titer of *M. penetrans* as the active ingredient, and may also contain one or more of a pH adjuster, buffer, stabilizer, excipient and/or an additive for rendering the solutions isotonic. The injectable solutions may be prepared to be adapted for subcutaneous, intramuscular or intravenous injection by conventional techniques. If desired, the solutions may be lyophilized in a usual manner to prepare lyophilized injections.

The dosage of *M. penetrans* administered will, of course, depend on the mode of administration and the interval of administration. An optimal dose of the active ingredient and an optimal interval of administration can easily be determined by routine preliminary tests known in the art.

The antigens of mycoplasmas which share antigenic determinants with *M. penetrans* can also be used as vaccines to induce the formation of protective antibodies or cell-mediated immunity to *M. penetrans*. It is believed that antigens of other mycoplasmas share many antigenic determinants with *M. penetrans,* but lack the pathogenicity of *M. penetrans*. Other mycoplasmas useful in vaccines against *M. penetrans* can be determined using conventional techniques for comparing antigenic similarity or cross reaction and nucleotide sequences for sequence homology.

In addition to AIDS, *M. penetrans* may be implicated in a number of other disease states including Chronic Fatigue Syndrome, Wegener's Disease, sarcoidosis, respiratory distress syndrome, Kikuchi's disease, autoimmune diseases such as collagen vascular disease and lupus, "slow virus" diseases and chronic debilitating diseases such as Alzheimer's Disease. *M. penetrans* may be either a causative agent of these diseases or a key co-factor in these diseases.

Furthermore, since the presence of *M. penetrans* is most often associated with AIDS and other sub-acute or acute fulminant disease states and more profoundly affects the course of its disease, it can be used to determine the prognosis of these diseases, which information can be utilized for designing therapy regimes.

*M. penetrans* is potentially sensitive to a number of antibiotics, including doxycycline, tetracycline, and quinalones such as ciprofloxacin or ofloxacin. Therefore, effective treatment of any of the above implicated diseases should include administration of antibiotics to which *M. penetrans* is sensitive.

When using the effective antibiotics as the active ingredients of pharmaceutical compositions, the pharmaceutical compositions may be administered by a variety of routes including oral, intravenous, aerosol and parenteral. The amount of active ingredient (antibiotic) necessary to treat an *M. penetrans* infection will depend on the body weight of the patient, but will usually be from about 0.001 to about 100 mg/kg of body weight, two to four times daily.

The present invention is further illustrated by reference to the following examples. These examples are provided for illustrative purposes, and are in no way intended to limit the scope of the invention.

EXAMPLE 1

Isolation of *M. penetrans* from Patients with AIDS

All the urine specimens from $HIV^+$ patients in this study were collected in two AIDS clinics. Urine specimens from 38 $HIV^+$ patients were first obtained from clinic I. Later, urine specimens from 75 $HIV^+$ patients were obtained from a second clinic (clinic II) located in different geographic region over a period of 3 months. The 98 control urine specimens were obtained from age-matched $HIV^-$ healthy donors. For the repeated isolations from the first clinic I patient with *M. penetrans* infection, the urine specimens were purposely coded at the site of collection to verify each isolation.

Urine was collected in sterile containers and concentrated 10-fold by centrifugation (3000×g for 15 minutes at 4° C.) and resuspended in 1/10 of the original urine. The resulting urine sediments were cultured after serial 1:10 dilutions in modified SP-4 media (Tully, J. G., et al., *Science* 195, 892 (1977); Lo, S-C., et al., *Am J. Trop. Med. Hyg.* 41, 586 (1989)) (glucose 0.1% and arginine 0.01%) in 12×75 mm tissue culture tubes, incubated at 37° C. aerobically and in GasPak jars (BBL, Micro. Sys. Cockeysville, Md.) anaerobically, and observed daily for a change in color. Tubes showing color change were inoculated onto 60 mm petri dishes containing 5 ml of modified SP-4 agar (1%).

The mycoplasma from the initial patient at clinic I was triple cloned by passing a broth culture through 220 nm membrane filter, incubating the filtrate on SP-4 agar for 10–14 days at 37° C. and isolating a well formed single colony. This mycoplasma was also examined for possible bacterial reversion by passing the organism 5 times in antibiotic-free medium. The organism was then studied for cell wall formation under electron microscopy (E.M.) and also subcultured to conventional blood agar for bacterial colony examination after 72 hours at 37° C.

The urine sediments from one HIV+ male homosexual patient at clinic I grew M. penetrans with an estimated titer of $10^5$/ml urine. This patient remained asymptomatic, without Kaposi's sarcoma or any opportunistic infection, but did have persistant low $CD_4^+$ lymphocyte counts ($<100\times10^6$/ liter) during the previous two years. SP-4 broth cultures of the patient's urine sediments appeared slightly turbid, and the pH shifted markedly to acid after 8 to 10 days incubation. It was found that anaerobic conditions slightly improved growth of M. penetrans. M. penetrans was repeatedly isolated in high titers from the urines of this patient in all six subsequent attempts over four months. M. penetrans was also isolated from the urine of five other HIV+ patients from clinic II. The control urines from 98 HIV− patients did not contain M. penetrans.

EXAMPLE 2

CharaCterization Of properties of M penetrans

Hemadsortion of human red blood cells (RBC) was examined after incubating 0.5% of RBC (type O, Rh-) suspension in PBS with the fried egg colonies of M. penetrans from Example 1 on the agar plate at 37° C. for 30 minutes. Cytadsorption was similarly studied by incubating PBS suspensions ($10^5$/ml) of $CD_4^+$ human lymphocytes (CEM cells, ATCC CCL 119) or human monocytic cells (U937 cells, ATCC CRL 1593) with M. penetrans colonies from Example 1 on the plate at 37° C. for 30 minutes. Attachment and penetration of M. penetrans into Vero monkey kidney cells, mouse NIH/3T3 fibroblasts, transformed human embryonal kidney cells (ATCC CRL 1572), cervical carcinoma cells (Hela), normal human umbilical endothelial cells, CEM human lymphocytes and U937 human histiocytic cells were studied by introducing $10^7$ CFU M. penetrans onto a monolayer or a suspension culture in 75 cm$^2$ flask. The cultures were fixed with 2% glutaraldehyde 24–48 hours later, processed and ultra-thin sectioned for E.M. examination.

M. penetrans adhered to the surface of plastic or glass culture flasks, a characteristic termed adhesion. The organism showed a tendency to form microspherules which also firmly adhered on the flask surface (FIG. 4A). Inoculation of M. penetrans into suspension cultures of human $CD_4^+$ lymphocytes (CEM) or human monocytic cells (U937) rapidly induced cell aggregation (FIG. 4B). The fried egg colonies of M. penetrans on the agar plates revealed a strong property of hemadsorption for human, guinea pig and rabbit red blood cells (RBC) (FIG. 4C). Cytadsorption of human $CD_4^+$ CEM cells and U937 human monocytes to the M. penetrans colonies was also highly significant (FIGS. 4D and E). In comparison, the parallel study revealed M. hominis colonies did not possess any cytadsorption property for either the CEM human lymphocytes or U937 human monocytes (FIG. 4F).

Electron microscopy (E.M.) with negative staining showed most M. penetrans organisms were rod-like, 0.2 to 0.4 μm wide and 0.8 to 2.0 μm long, and had two distinct compartments. These were a densely packed tip-like structure and a more loosely packed body (FIG. 1A). Occasional branching organisms were found. E.M. of ultra-thin sectioned organisms also revealed two sharply divided compartments internally, bound only by a single triple layered unit membrane (FIG. 1B). The compartment forming the tip-like structure was densely packed with very fine granules (F). The broader compartment or the body was filled with loosely packed coarse granules (C) consistent with ribosomal structures. Culture of M. penetrans in antibiotic-free media did not promote cell wall formation. The unusual structural compartmentation has never been found in mycoplasmas with the single possible exception of M. iowae. This pathogenic avian mycoplasma was reported to have fine and coarse granule compartments. Mirsalimi, S. M., et al., Avian Dis. 33, 310 (1989).

Infections of human and non-human mammalian cell cultures with M. penetrans produced a varying degree of cytopathic effects. Monolayer cultures of NIH/3T3 cells (mouse fibroblasts), Vero cells (monkey kidney cells), human endothelial cells, transformed human renal cells and cervical carcinoma cells (Hela cells) were all found to be highly susceptible to infections with M. penetrans. Typical cytopathic effect with profound degenerative changes occurred in 2–4 days. FIG. 5 shows the profound cytopathic changes of Vero cells following M. penetrans infection. No apparent cell-type specificity was found in this process. Infections of human lymphocyte and monocyte cultures with M. penetrans also produced similar cytopathic effect. However, in general, suspension cultures were less susceptible than monolayer cultures to M. penetrans infections. Presumably it is because of the strong surface attachment property of the mycoplasma that the spread out monolayer cells covering the culture flask surface are affected more profoundly. Different cell lines also revealed different degrees of sensitivity. Between the two $CD_4^+$ human lymphocyte cell lines tested, Molt-4 cells appeared to be much more susceptible than CEM cells.

E.M. of the M. penetrans infected cultures showed many "foci" of heavy infection. Each focus of infection consisted of a large number of organisms attacking a single cell and leaving the neighboring cells in the cultures unaffected (FIG. 6A). Adhesion on the surface of human or non-human cells was followed by active invasion of M. penetrans into the cytoplasm of these cells (FIG. 6B). The organisms used their tip-like structure or the compartment with densely packed fine granules (F) as "spearheads" in the process of invasion. Thus, many organisms were caught in the middle of this process with their spearheads deeply buried in the cytoplasm of the cell which they were actively attacking (FIG. 6B). Insertion or piercing of the organism's tip compartment into the cell resulted in deep invagination of the cell membrane. Entire organisms could completely invade into the cells without penetrating through cell membrane. Most of the intracellular mycoplasmas were found in membrane bound vacuoles in the cytoplasm (FIG. 6C). Although many cells loaded with the invaginated mycoplasmas still appeared to be intact, cell disruption and necrosis following extensive invasion of M. penetrans eventually occurred (FIG. 6D).

In order to find if the organism indeed applied the same pathobiological mechanism documented in vitro in the infection of a patient's urogenital tract, urine sediments of the M. penetrans infected patient from Clinic I were studied. Cultures of sediment revealed $10^5$/mL M. penetrans, without other bacterium or mycoplasma being found. Structurally unique M. penetrans could be directly identified in the sediments by E.M. Organisms with typical morphology were captured at different stages of invading epithelial cells in the urine sediments (FIG. 7A). Intracellular organisms were also identified in membrane bound vacuoles in cytoplasm of these epithelial cells sloughed from the patient's urogenital tract (FIG. 7B). The presence of microvilli identifies these epithelial cells as renal tubular cells or urothelial cells.

EXAMPLE 3

Preparation of *M. penetrans* Antigens

*M. penetrans*, as isolated in Example 1 was prepared by pelleting logarithmic-phase cultures and washing twice with ice-cold 1×PBS, pH 7.2 (Biofluids, Inc., Rockville, Md.; catalogue no. 310). The cell pellets were stored at −70° C. before use. Triton X-114 (TX-114) was purchased from Boehringer Mannheim Corporation, Indianapolis, Ind. (catalogue no. 1033441), and diluted to 10% (vol./vol.) with sterile deionized water. The mycoplasmas were subjected to TX-114 phase partitioning by a modification of the method originally described by Bordier, C., *J. Biol. Chem.* 256, 1604 (1981) which was subsequently adapted to mycoplasmas as described by Wise, K. S., et al., *J. Bacteriol.* 169, 5546 (1987); Bricker, T. M., et al., *Infect. Immun.* 56, 295 (1988); Rosengarten, R., et al., *Science* 247, 315 (1990). The cell pellets from 200 ml cultures were resuspended in 0.8 ml ice-cold 1×PBS, pH7.2, transferred to a 1.5 ml polypropylene microcentrifuge tube (Marsh Biomedical Products, Rochester, N.Y.), and sonicated for 10–15 seconds at 80% duty cycle with power output setting at 7 by using the sonicator with cup horn attachment (Heat System-Ultrasonics, Inc., Farmingdale, N.Y.). The cells were solubilized by adding TX-114 to a final concentration of 2% (v/v), incubating in ice for 30 minutes with occasional mixing, and continuing incubation for another 90 minutes after addition of NaCl to 0.35M. The lysates were centrifuged at 0° C. for 10 minutes at 14,263×g, and the supernatant was transferred to a new tube and centrifuged one more time under the same conditions. The supernatant was collected, incubated in a 37° C. water bath for 5 minutes to induce condensation of TX-114, and then centrifuged at 30° C. for 5 minutes at 11,269×g. The resulting heavy, detergent-enriched fraction (TX-114 phase, 0.1–0.2 original total volume) was saved and readjusted to the original volume with ice-cold 1×PBS, pH7.2, plus 0.35M NaCl. The solution was thoroughly mixed by vortexing, left in ice for 10 minutes and then repartitioned as described above. After three cycles of phase fractionation, the condensed TX-114 phase was adjusted to the original volume (1 ml) with 1×PBS, pH7.2, incubated in an ice bath for 1 hour with occasional mixing, and then centrifuged at 0° C. for 10 minutes at 14,263×g. The supernatant was saved, designated as TX-114 extract, and used as antigens for ELISA and Western blot analyses described in Examples 4 and 5.

EXAMPLE 4

Western Blot with Partially Purified M. petetrans Antigens

Proteins (about 200 μg) from the TX-114 extract of Example 3 were separated by SDS-PAGE (Laemmli, U. K., *Nature* 227, 680 (1970)) on a 10% 0.75 mm gel, and electroblotted on a BA-85 nitrocellulose membrane (Schleicher & Schuell Inc., Keene, NH). The membrane was blocked with 3% non-fat dry milk in 1×PBS, pH7.2, for 30 minutes, rinsed twice with 1×PBS, air dried, and cut into 0.4 mm strips for subsequent Western blot analysis. Towbin, H., et al., *Proc. Natl, Acad. Sci. USA* 76, 4350 (1979). Each strip was preincubated for 5 minutes with 2 ml diluent containing 10% normal goat serum—2% BSA—0.1% NP-40—1×PBS (diluent I), and 0.02% sodium azide, then serum was added to a final dilution of 200 fold. The reaction was carried out at 25° C. for 15 hours with continuous shaking, and then stopped by aspirating the fluid and washing the strips 6 times with 1×PBS, pH7.2, 0.5% NP-40. Following incubation with 1:1,000 diluted biotin-labeled antibody of goat anti-human IgG (r) and subsequent incubation with 1:5,000 diluted peroxidase-labeled streptavidin in diluent I for 90 minutes each at 25° C., the strips were developed at 37° C. for 15 minutes with 4-chloro-1-naphthol peroxidase substrate system (Kirkegaard & Perry Laboratories, Inc., Gaithersburg, Md.).

Figure 8:
FIG. 8 shows a Western blot analysis of human antibody response against partially purified *M. penetrans* surface antigens. Lanes 1–8 show sera derived from eight different healthy blood donors. Lanes a–u show sera or plasma from 20 different individuals with a positive HIV antibody test by ELISA. Arrows indicate the positions of prestained protein markers with apparent molecular weights of 205 k, 103 k, 67 k, 42 k and 28 k, respectively, from top to bottom.

Western blot analysis of human antibody response against the *M. penetrans* antigens was then observed as presented in FIG. 8. Lanes 1–8 show sera derived from 8 different healthy blood donors. In contrast, Lanes a–u show sera or plasma from 20 different individuals with a positive HIV antibody test by ELISA. These individuals also showed positive antibody response against *M. penetrans* antigens by our newly developed ELISA. Lanes a & b show sera from different bleeding dates of the same individual. Lanes a, d, and e were individuals with positive growth of *M. penetrans* from their urine cultures. Arrows indicate the positions of prestained protein markers with apparent molecular weight from top to bottom of 205 k, 103 k, 67 k, 42 k, and 28 k, respectively.

EXAMPLE 5

ELISA with Partially Purified *M. penetrans* Antigens

The TX-114 extract from Example 3 was diluted 1:100 in 1×PBS, pH7.2 (PBS), at a protein concentration of about 3 μg/ml, and coated on Nunc-Immuno F96 MaxiSorp w/certificate plates (Nunc Inc., Naperville, Ill.) at 37° C. for 5 hours in a humid chamber with 100 μl aliquot in each well. Following overcoating with 2% BSA plus 0.02% sodium azide at 25° C. for 2 hours and washing twice with PBS plus 0.05% NP-40 (solution A), each well received 100 μl of 1:100 diluted human sera or plasma in a diluent containing 10% normal goat serum, 2% BSA, 0.3% NP-40, and PBS. The reaction was carried out at 5° C. overnight, then 37° C. for 90 minutes, and stopped by aspirating the excess fluid and washing the plates six times with solution A. Subsequently, each well was incubated with 100 μl of 1:1,000 diluted biotin-labeled antibody of goat anti-human IgG (r) in a solution containing 10% normal goat serum, 2% BSA, 0.1% NP-40, and PBS (diluent 1) at 37° C. for 90 minutes, washed as described above, and then incubated with 100 μl of 1:20,000 diluted peroxidase-labeled streptavidin in diluent I at 37° C. for 90 minutes. After washing the plates as described above, each well was developed with 100 μl of ABTS peroxidase substrate solution at 37° C. for 10 minutes, and the reaction was stopped by mixing with 100 μl of 1% SDS solution. The optical density at 405 nm corrected with a reference wavelength at 650 nm was measured by a microplate reader from Molecular Devices Corporation, Menlo Park, Calif., with automatic subtraction of the OD of the blank.

Figure 9:
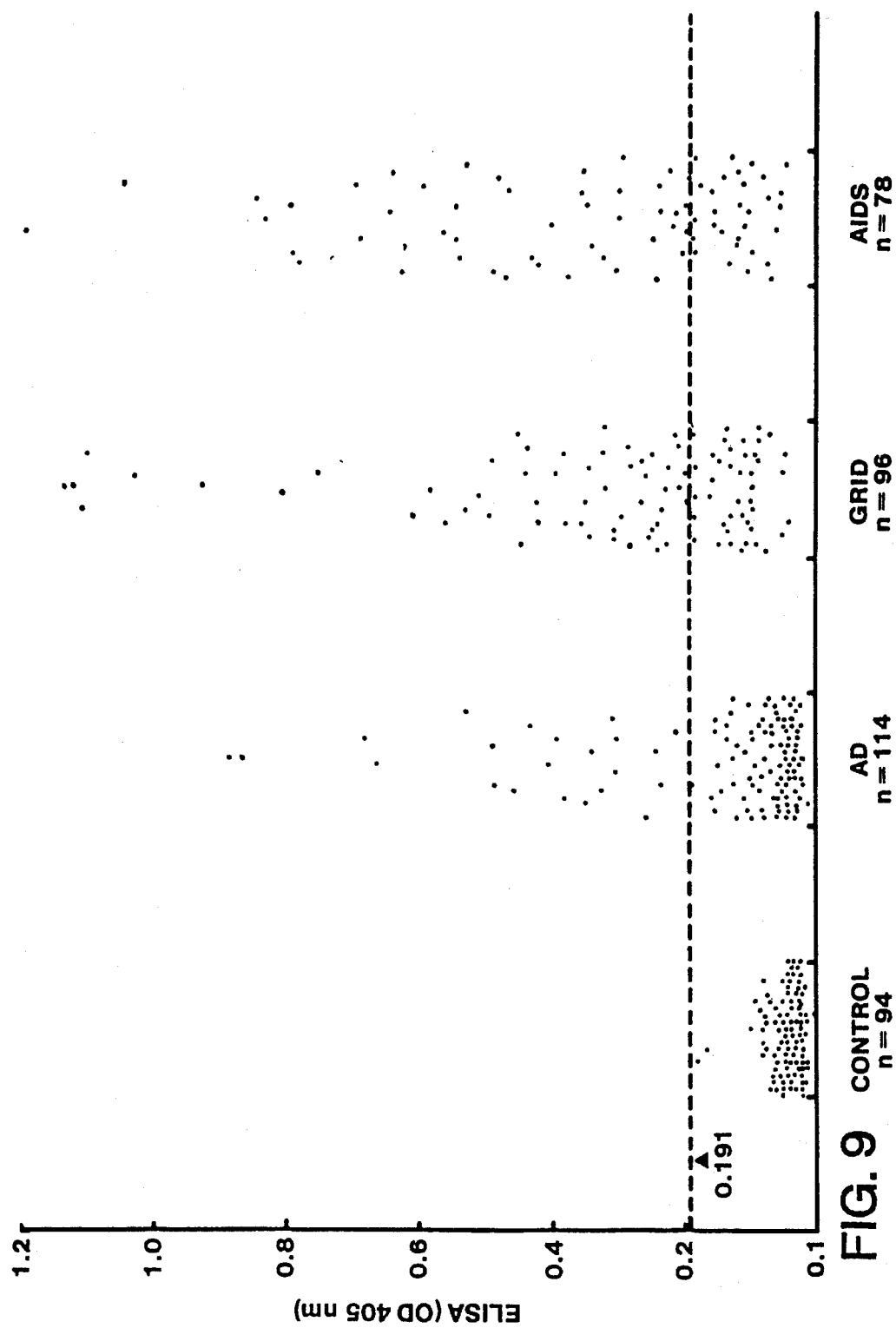
FIG. 9 shows a comparison of the immuno-response to partially purified *M. penetrans* surface antigens by ELISA between healthy blood donors (CONTROL) and HIV-1 positive patients (AD, GRID, AIDS). Three groups of patients are shown with the number of sera tested in each group designated by "n=". The line across the area with optical density (OD) at 0,191 was the cutoff line of the ELISA test for *M. penetrans*.

A comparison was made of the immuno-response to *M. penetrans* antigens by ELISA between healthy blood donors (negative controls) and HIV-1 positive patients as shown in FIG. 9. For patients with positive HIV-1 ELISA test, three groups originally involved in three different studies were included and indicated as AD (HIV$^+$ asymptomatic donors), GRID, and AIDS respectively. The numbers of sera tested from different individuals in each group were shown as "n=". The line across the area with optical density (OD) at 0.191 was the cutoff line of the ELISA test for *M. penetrans*. This cutoff value was the sum of the mean value plus the value of 5 standard deviation derived from 94 healthy blood donors. The percentage of samples tested in each group with OD readings above cutoff was 0%, 19%, 62%, and 56% for negative controls, AD (HIV$^+$ asymptomatic donors), AIDS, and two groups of AIDS patients referred to as GRID, respectively.

EXAMPLE 6

Antigenic Comparison of *M. penetrans* with Other Mycoplasmas

The antigenic comparison of different species of mycoplasmas using immunoblots was performed as previously described in detail. Lo, S-C.,., et al., *Am. J. Trop. Med. Hyg.* 41 586 (1989). Each of the immunoblots was immunostained with polyclonal rabbit antiserum raised against one of the human mycoplasmas. Immunofluorescence assays using these polyclonal antibodies specific for each of the human mycoplasmas were also studied as previously described. Id. The 6A1 clone of *M. penetrans* was used to prepare rabbit antiserum in the study. The titer of 6A1 *M. penetrans* specific hyperimmune rabbit antiserum was $5\times10^4$, shown in the ELISA.

*M. penetrans* was found to be antigenically different from any of the other human mycoplasmas. The polyclonal rabbit antibody raised against each of the human mycoplasmas, *M. fermentans* (incognitus strain and PG-18), *M. pirum*, *M. pneumoniae*, *M. genitalium*, *M. orale*, *M. salivarium*, *M. hominis* and *Acholeplasma laidlarvii*, did not react with *M. penetrans* in a dot-blot immunochemical assay or in an immunofluorescence assay. Furthermore, rabbit antiserum raised against *M. penetrans* failed to react with the other human mycoplasmas in the assay.

EXAMPLE 7

DNA Comparison of *M. penetrans* with Other Mycoplasmas

In DNA analyses, the procedures for mycoplasma DNA preparation and hybridization were performed as previously described. Id. All the human mycoplasmas were originally obtained from American Type Culture Collection (ATCC). In addition, *M. alvi*, *M. Sualvi*, *M. iowae*, *M. moatsii*, *M. pirum*, *M. fermentans* (PG18 strain), *M. buccale* and *M. spermatophilum* were kindly provided by J. G. Tully, NIAID, NIH. Three recombinant DNA clones (M6A1-3.2, M6A1-3.1 and M6A1-2.9) were constructed by ligation of DNA fragments from EcoRI digestion of the *M. penetrans* 6A1 DNA into vector DNA M13mp19 and subsequent transformation into *E Coli* DH5 F'IQ cells (Yanisch-Perron, C., et al., *Gene* 33, 103 (1985) (Gibco BRL, Gaithersburg, Md.). The plaques were screened by probing with $^{32}$P-labeled *M. penetrans* genomic DNA. Three positive clones (carrying 3.2, 3.1 and 2.9 kb inserts, respectively) were selected and their insert DNAs were purified. *M. penetrans* 6A1 DNA and the three cloned insert DNAs were radiolabelled by the random primer extension method (Feinberg, A. P., et al., *Anal. Biochem.* 132, 6 (1983) and used as probes. The blot III in FIG. 3B was reprobed with $^{32}$P-labelled cDNA of *E. coli* r-RNA (blot IV), after removing the previously incorporated M6A1-2.9 probe by boiling the filter. Lo, S-C., et al., *Am. J. Trop. Med. Hyg.* 40, 213 (1989). After hybridization, all the membranes were washed at 64° C. for 20 minutes each in 2×SSC, 0.5% SDS before autoradiography.

$^{32}$P-labeled genomic DNA from *M. pentrans* was used as probe and hybridized with DNA from other human mycoplasmas and animal mycoplasmas known to utilize both glucose and arginine. There was no significant DNA homology (FIG. 3A). The same mycoplasma had been isolated from urines of the patient from clinic I in each of the subsequent six isolation attempts. The identity of all six subsequent isolates was confirmed by the morphological, biochemical, antigenic, and DNA analyses (FIG. 3A, lanes m, n, o, p). Southern blot analysis using $^{32}$P-labeled recombinant DNAs (M6A1-3.2, M6A1-3.1 and M6A1-2.9) molecularly cloned from *M. penetrans* as probes also revealed lack of homology between *M. penetrans* and other species of human mycoplasmas and animal mycoplasmas with the same biochemical properties (FIG. 3B). The characteristic restriction enzyme mappings of r-RNA genes in the mycoplasma group often enable the identification of related species. The EcoRI restriction pattern of r-RNA genes for *M. penetrans* was different from any of those mycoplasmas tested (FIG. 3B-IV).

EXAMPLE 8

Vaccine Containing Inactivated or Attenuated *M. penetrans*

Sixteen chimpanzees are divided into four groups. Group A is inoculated intravenously with 1 ml of *M. penetrans* as isolated in Example 1. Group B is inoculated with 1 ml of fluid containing $10^6$ *M. penetrans*-infected mammalian cells. Group C is inoculated with 1 ml of fluid containing $10^6$ inactivated or attenuated *M. penetrans*, and Group D is the control group and did not receive an inoculation of the infected mammalian cells.

All chimpanzees in Groups A and B developed symptoms of AIDS. However, none of the chimpanzees in Groups C and D developed the symptoms of AIDS. The chimpanzees of Group C are rendered immune to subsequent challenge of intravenous inoculation with 1 ml of *M. penetrans* or 1 ml containing $10^6$ *M. penetrans*-infected NIH/3T3 cells.

EXAMPLE 9

PCR Assay for *M. penetrans*

An assay of urine sediments prepared in Example 1 is illustrative of a PCR assay. The amplification of selective DNA sequences was performed with thermostable Taq DNA polymerase (Native Taq; Perkin Elmer Cetus, Norwalk, Conn.) (10) in the automated Perkin-Elmer Cetus DNA thermal cycler (Norwalk, Conn.). One ml of urine sediment prepared and filtered as described in Example 1×was first centrifuged at 1,500×g for 15 min. Nine-hundred µl of the supernatant was removed. Proteinase K was added to the remaining 100 µl sample (final concentration of 200 µg/ml) and the sample was digested at 56° C. for 2 hrs.

Before PCR analysis, the digested samples were heated at 95° C. for 10 min. Each 10 µl urine sediment sample to be amplified was adjusted to a total volume of 160 µl with PCR buffer containing a final concentration of 50 mM KCl, 20 mM Tris-HCl (pH 8.3), 1 mM MgCl$_2$, 0.001% gelatin, each primer (forward primer RW-010 (SEQ ID NO:4) and reverse primer RW-011 (SEQ ID NO:5)) at 0.5 µM, each dNTP at 250 µM and 2.5 U of Taq DNA polymerase. The samples were overlaid with 3 drops of mineral oil (50 µl).

Samples were denatured at 94° C. for 35 sec, annealed to the primers at 56° C. for 45 sec, and extended at 72° C. for 1 min. The annealing time was increased by one sec/cycle during the amplification. After the final cycle, the annealing time was increased to 5 min, followed by extension for 5 min. Twenty μl aliquots from each amplified sample were removed and analyzed on a 6% polyacrylamide gel in 1×Tris-borate-EDTA buffer (Maniatis et al., *Molecular Cloning: a laboratory manual.* Cold Spring Harbor Laboratory, Cold Spring Harbor, N.Y. (1982)). The gels were stained with ethidium bromide and the DNA visualized by UV fluorescence. The fractionated DNA was electroblotted onto a Zeta-Probe membrane (Bio-Rad, Richmond, Calif.) at 100 volts for 2 hrs., in 0.5×Tris-acetate-EDTA buffer (Maniatis et al., Supra), followed by denaturation and fixation in 400 mM NaOH, 2 mM EDTA for 10 min. at room temperature. The Zeta-Probe membrane was rinsed 3 times with 2×SSC in 20 mM Tris-HCl (pH 7.5) and air dried for 10 min. Prehybridization was carried out in 30% formamide, 4×SSC, 5×Denhardt's, 20 mM Tris-HCl, (pH 7.5), 2 mM EDTA, 1% SDS and 350 μg/ml of denatured salmon sperm DNA at 30° C. Hybridization was in the same mixture but containing the oligonucleotide probe RW-012 (SEQ ID NO:3) which was 5' end labeled with $^{32}$P-ATP, and was conducted overnight at 30° C. After hybridization the membrane was washed at 45° C. in 2×SSC, 0.5% SDS four times (30 min. each).

Fifty urine sediments obtained from HIV positive patients and twelve urine sediments obtained from HIV negative healthy control individuals were tested for the presence of *M. penetrans* specific DNA sequences by using the PCR assay. Primer pairs of synthetic oligonucleotides, designated RW-010 (SEQ ID NO:4) and RW-011 (SEQ ID NO:5) were used to amplify a 195 bp segment of the *M. penetrans* DNA. Six of fifty urine sediments obtained from HIV positive patients with varying stages of AIDS disease, tested positive for the presence of *M. penetrans* DNA. In contrast, none of the twelve urine sediments obtained from HIV negative non-AIDS controls tested positive. Table II below, shows the PCR results. The RW-012 (SEQ ID NO:3) probe hybridized strongly to all positively amplified samples.

Specificity of the reaction was also examined by attempting to amplify the DNAs isolated from other human or non-human mycoplasmas, common tissue culture contaminating mycoplasmas, Gram-positive or Gram-negative bacteria, mouse, monkey and human cell culture and/or tissue. The reaction does not produce the specific 195 bp DNA fragment (Table II).

The primers and probe used in this Example are:
Forward primer, RW-010 (SEQ ID NO:4):
  5'-ATG GGG CTT CTA GAT TTT TTG CT-3'
Reverse primer, RW-011 (SEQ ID NO:5):
  5'-CAG AAA CTA GCT TTA CTT CTT CA-3'
Probe, RW-012 (SEQ ID NO:3):
  5'-GAA GAT GAA ATC GAT GAC ACA GAA-3'

TABLE 2

PCR Detection of *M. penetrans*

| Sources | Concentration of DNA tested | Positivity |
|---|---|---|
| *M. penetrans* | 2 fg | + |
| Mycoplasmas | | |
| *M. alvi* | 10 ng | − |
| *M. fermentans* | 10 ng | − |
| *M. genitalium* (ATCC 33530) | 10 ng | − |
| *M. hominis* (ATCC 15488) | 10 ng | − |
| *M. moatsii* | 10 ng | − |
| *M. orale* (ATCC 23714) | 10 ng | − |
| *M. pneumoniae* (ATCC 15531) | 10 ng | − |
| *M. Salivarium* (ATCC 23064) | 10 ng | − |
| *M. sualvi* | 10 ng | − |
| *M. prium* | 10 ng | − |
| *Acholeplasma laidlawii* (ATCC 23206) | 10 ng | − |
| *Ureaplasma urealyticum* (ATCC 27618) | 10 ng | − |
| Bacteria | | |
| *Escherichia coli* | 100 ng | − |
| *Clostridium perfringens* | 100 ng | − |
| Each of 10 normal donor PBMC** | 1 μg | − |
| Each of 4 placentas (normal delivery) | 1 μg | − |
| Each of 2 mouse spleens | 1 μg | − |
| Urine sediments* from each of 12 normal non-AIDS blood donors | 10 μl | − |
| urine sediments from HIV$^+$ patients with AIDS | | |
| GTU-54 | 10 μl | + |
| TX 270 | 10 μl | + |
| TX 343 | 10 μl | + |
| TX 662 | 10 μl | + |
| TX 682 | 10 μl | + |
| TX 984 | 10 μl | + |

*All the urine sediments (10 μl) were pre-digested with Proteinase K.
**PBMC: Perirpheral Blood Mononuclear Cells. All the AIDS urine sediments PCR positive for *M. penetrans* were confirmed by culture isolations.

While the invention has been described in connection with specific embodiments thereof, it is understood that it is capable of further modifications. The description of the invention is intended to cover any variations, uses or adaptations of the invention following, in general, the principles of the invention, and including such departures from the present disclosure as come within known and customary practice within the art to which the invention pertains.

What is claimed is:

1. An antibody which specifically reacts with the mycoplasma designated ATCC 55252.

2. A method for the detection of antibodies which specifically bind to an antigenic site of a mycoplasma designated ATCC 55252 in samples of body tissues, cells and fluids comprising the steps of:
   (a) contacting an antigen with said sample; and
   (b) measuring the formation of antigen-antibody complex; said antigen selected from the group consisting of antigens isolated from a mycoplasma designated ATCC 55252 by sonication and detergent extraction.

3. A method for the detection of antigens of the mycoplasma designated ATCC 55252 in samples of body tissues, cells and fluids comprising reacting the antibody of claim 1 with said sample and measuring the formation of antigen-antibody complex.

4. A diagnostic kit for the detection of mycoplasma-specific antibodies comprising or slide, an antigen and means for detecting an antigen-antibody complex, said antigen selected from the group consisting of antigens isolated from a mycoplasma designated ATCC 55252 by sonication and detergent extraction.

5. A diagnostic kit for the detection of an antigen of the mycoplasma designated ATCC 55252 comprising a container or slide, the antibody of claim 1 and means for detecting an antigen-antibody complex.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 276 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
  (A) ORGANISM: Mycoplasma penetrans (xi) SEQUENCE DESCRIPTION: SEQ ID NO:1:

```
GAATTCAAGA AGATAAAAAT AAGTTATATT TTACTATTCT TGATTTTAAT GGGGCTTCTA    60
GATTTTTTGC TGATGAAAAA TTTAATGGTC CAGAAATAAA AAGCTTAGAT TATGATTTAA   120
AAGATTTTAC AGGTGATGGT TTTACTTATA ATTTTCCTGA AGATGAAATC GATGACACAG   180
AAGATGGGAT TGAAACAAGA AAGAAAATTT ATGTTAATAG TGAAGAAGTA AAGCTAGTTT   240
CTGAAATTAA ACAATACTAT GATGAAGAAG GTAAAA                             276
```

(2) INFORMATION FOR SEQ ID NO:2:

(i) SEQUENCE CHARACTERISTICS:
    (A) LENGTH: 308 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Mycoplasma penetrans (xi) SEQUENCE DESCRIPTION: SEQ ID NO:2:

```
GAATTCTTCT ACAACATCTA GTATTGATTA CACTGGAATG AAAGCTAGTA AATTTATAAG    60
TAGTTTTTAT AATGGTCAAA CTAATAGTTA TGATAACTTT TTAAAAGCGT TTGATTTAGT   120
AAAACTACCA ACTAATACAT CTGCAATTAA TTATTACTAT ATAAGTGATG TTCAATTAAC   180
AAGTGATGAT GTTAATGGAA CAGTAACTAT ATATTACACA TTCACATTCC CAAATGCTGG   240
AGATGTAGAA GGTAGCTCAT CTACTTCTTC AATTATCTTA AGTGGCTTTT TAACTAATCA   300
ATCTTTTT                                                             308
```

(2) INFORMATION FOR SEQ ID NO:3:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: RW-012 probe (xi) SEQUENCE DESCRIPTION: SEQ ID NO:3:

```
GAAGATGAAA TCGATGACAC AGAA                                           24
```

-continued ( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: RW-010 forward primer ( x i ) SEQUENCE DESCRIPTION: SEQ ID NO:4:

ATGGGGCTTC TAGATTTTTT GCT        23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: RW-011 reverse primer ( x i ) SEQUENCE DESCRIPTION: SEQ ID NO:5:

CAGAAACTAG CTTTACTTCT TCA        23